(12) United States Patent
Shin et al.

(10) Patent No.: US 8,030,466 B2
(45) Date of Patent: Oct. 4, 2011

(54) 3'-O-FLUORESCENTLY MODIFIED NUCLEOTIDES AND USES THEREOF

(75) Inventors: Dongyun Shin, Seoul (KR); Dae-ro Ahn, Seoul (KR); He-Chul Ahn, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 12/605,672

(22) Filed: Oct. 26, 2009

(65) Prior Publication Data
US 2011/0076679 A1  Mar. 31, 2011

(30) Foreign Application Priority Data
Sep. 29, 2009  (KR) .................. 10-2009-0092296

(51) Int. Cl.
| C07H 21/00 | (2006.01) |
| C07H 21/02 | (2006.01) |
| C07H 21/04 | (2006.01) |
| C12Q 1/68 | (2006.01) |
| C12P 19/34 | (2006.01) |

(52) U.S. Cl. .................. 536/23.1; 536/24.3; 536/24.33; 536/25.3; 536/26.6; 435/6; 435/91.1; 435/91.2; 422/61

(58) Field of Classification Search .............. 435/6, 91.1, 435/91.2; 536/23.1, 24.3, 24.33, 25.3, 26.6; 422/61
See application file for complete search history.

(56) References Cited

U.S. PATENT DOCUMENTS
| 5,798,210 A | 8/1998 | Canard et al. |
| 7,105,300 B2 | 9/2006 | Parce et al. |
| 7,279,563 B2 | 10/2007 | Kwiatkowski |

FOREIGN PATENT DOCUMENTS
WO  WO 00/50642  * 8/2000

OTHER PUBLICATIONS

Guo et al. (Jul. 8, 2008) "Four-Color DNA Sequencing with 3'-O-Modified Nucleotide Reversible Terminators and Chemically Cleavable Fluorescent Dideoxynucleotides," *Proc. Nat. Acad. Sci. USA* 105(27):9145-9150.
Metzker et al. (1994) "Termination of DNA Synthesis by Novel 3'-Modified Deoxyribonucleoside 5'-Triphosphates," *Nuc. Acids Res.* 22(20):4259-4267.
Shendure et al. (May 2004) "Advanced Sequencing Technologies: Methods and Goals," *Nat. Rev. Genet.* 5:335-344.
Southworth et al. (May 1996) "Cloning of Thermostable DNA Polymerases from Hyperthermophilic Marine Archaea with Emphasis on *Thermococcus* sp. 9° N-7 and Mutations Affecting 3'-5' Exonuclease Activity," *Proc. Nat. Acad. Sci. USA* 93:5282-5285.
Welch et al. (1999) "Syntheses of Nucleosides Designed for Combinatorial DNA Sequencing," *Chem. Eur. J.* 5(3):951-960.

* cited by examiner

*Primary Examiner* — Jezia Riley
(74) *Attorney, Agent, or Firm* — Ladas & Parry LLP

(57) ABSTRACT

The present invention relates to a DNA sequencing method using a nucleoside triphosphate with a fluorescent blocking group on its 3'-OH end as a reversible terminator. Further, the present invention relates to sequencing-by-synthesis method using the mono-modified reversible terminator (MRT), the novel nucleotide monomer having a reversible fluorescent blocking group removable chemically or enzymatically at its 3'-OH end. The sequencing method of the present invention facilitates sequencing of bases inserted by terminating extension of a nucleotide chain by the nucleotide monomer and then detecting fluorescence signal from 3'-OH end. At this time, after analyzing the fluorescence signal, the blocking group conjugated to the 3'-OH end can be effectively removed, indicating that a free 3'-OH functional group can be successfully restored, so that the next monomer insertion is possible, making continuous sequencing possible.

13 Claims, 4 Drawing Sheets

3'-O-FLUORESCENTLY MODIFIED NUCLEOTIDES AND USES THEREOF

CROSS-REFERENCE TO RELATED APPLICATIONS

This application claims priority of Korean Patent Application Serial No. 10-2009-0092296 filed Sep. 29, 2009, which is hereby incorporated by reference in its entirety to the extent not inconsistent with the disclosure herein.

BACKGROUND OF THE INVENTION

1. Field of the Invention

The present invention is drawn to a nucleoside triphosphate (3'-O-FL-dNTP) having a fluorescent 3'-O-blocking group which is chemically removable and a DNA sequencing method (sequencing-by-synthesis) using the same.

2. Description of the Related Art

By virtue of successful result of the Human Genome Project (HGP) recently completed, information of human genome could be obtained. Although this information contains common sequences of the human genome, it does not present individual variation in the genome. To acquire information of complete individual genomes, personal genomes have to be analyzed. Since the haploid human genome occupies approximately 3 billion DNA base pairs, if the capillary electrophoresis-based Sanger method, which has been widely used for DNA sequencing so far, is used for sequencing of a personal genome, the similar cost and time as required for the completion of the HGP will be needed to obtain information of the individual genome (G. M Church et al., Nature Reviews, 2004, 5, 335-344). Since 2004, the National Human Genome Research Institute (NHGRI, USA) has supported the development of technologies enabling whole genome sequencing of each individual with remarkably reduced costs, particularly at a cost of 100,000 dollars in a short term and 1,000 dollars in the long term. As a result, sequencing platforms capable of performing whole gemome sequencing of an individual at a cost of about 50,000 dollars are now commercialized. These machines are based on two major technologies, a pyrosequencing and a sequencing-by-synthesis (SBS). GS TLX Titanium series machine provided by 454 Life Sciences, a Roche Company is based on the pyrosequencing technology. It is possible to analyze 400-600 million bases for 10 hours and to analyze comparatively long chains (approximately 200 nucleotides) at once. However, Genome Analyzer provided by Solexa, Inc. is based on the SBS technology.

The sequencing-by-synthesis (SBS) which is directly related to the present invention, uses fluorescently labeled nucleotides. Particularly, according to the technology, each nucleotide is incorporated into a DNA primer by polymerases and then fluorescent signal from the nucleotide is detected to identify base of the nucleotide and the complementary base can be analyzed at the same time (see FIG. 2).

Nucleoside triphosphates (dNTPs) used for the SBS are basically dual-modified reversible terminators (DRTs), which are modified dNTPs having a reversible blocking group on the 3'-OH moiety (3'-O-blocking group) and a fluorophore on the base (see Figure, left). At this time, 4 bases (A, T, G, and C) are labeled with different fluorophores emitting lights of different wavelengths. A target DNA is used as a template for the polymerization using such modified dNTPs. Then, a nucleotide is once incorporated into a primer chain by DNA polymerases, the other dNTPs cannot be incorporated into the chain because of 3'-O-blocking group of the incorporated nucleotide. Then, the fluorescence of the fluorophore conjugated to the base of the incorporated nucleotide is detected to identify base of the incorporated nucleotide, leading to the analysis of the complementary nucleotide sequence of the template chain. When the fluorophore and the 3'-O-blocking group are removed, a free 3'-OH functional group is recovered, so that the next nucleotide can be incorporated. The base of the incorporated nucleotide can be identified by the same manner as described above, resulting in sequencing the template chain. This step by step sequencing is called 'sequencing-by-synthesis (SBS)'.

The dual-modified reversible terminators (DRTs) used for commercial SBS has a fluorescent group connected to a base via an acetylene linker. In that case, even though a 3'-O-blocking group and a fluorescent group are removed after DRT insertion and sequencing, the linker part connecting the fluorescent group to the base still remains. This remnant is called a molecular scar. As the sequencing progresses, a newly polymerized chain contains more molecular scars. Since such an accumulation of molecular scars reduces the activity and fidelity of polymerases later on, resulting in limiting the number of sequenced bases. Because of this problem, the SBS is known to have relatively short read-length ca. 25-35 bases, compared with pyrosequencing-based methods. Thus, this limit might increase chances of errors in profiling polynucleotides fragments when a long polynucleotide, which is cut into several short fragments for SBS, is analyzed.

There are two important factors to successfully perform the SBS. First, a polymerase capable of incorporating a DRT with almost perfect efficiency is required. Second, the fluorophore connected to a base and the 3'-O-blocking group have to be removed with almost perfect efficiency in aqueous solution without damaging DNA. Natural DNA polymerases have been evolved for long time so as to receive dNTPs having free 3'-OH selectively. Therefore, they do not accept a substrate when it has a blocking group at 3'-OH. In the earlier study, Sarfati et al. reported in 1994 that dNTPs having 3'-O-ester anthranylic blocking groups were incorporated in a DNA chain by many polymerases (AMV reverse transcriptase, Taq DNA polymerase, and Klenow fragment of DNA polymerase I) and then a free 3'-OH functional group could be recovered by cutting off ester bond using esterase to continue polymerization (Sarfati et al, Gene, 1994, 148: 1-6). In the same year, M. L. Metzker, et al. reported that they could observe the insertion of dNTPs having a 3'-OH group conjugated with different blocking groups by the action of polymerases (AMV reverse transcriptase, M-MuLV reverse transcriptase, Klenow fragment of DNA polymerase I, Sequenase, Bst DNA polymerase, AmpliTaq DNA polymerase, Vent(exo-) DNA polymerase, rTth DNA polymerase, and Pfu(exo-) DNA polymerase) and as a result, dNTPs having a 3'-O-methyl group and a 3'-O-(2-nitrobenzyl) group could be inserted via some of polymerases to terminate polymerization temporarily (M. L. Metzker et al., Nucleic Acids Research, 1994, 22: 4259-4267). However, those prior arts are not suitable to be used in the SBS with respect to efficiency and fidelity for the continuous polymerization.

The reason why dNTPs having a bulky 3'-O-blocking group cannot be accepted as a reaction substrate by polymerases might be explained by narrow space for the 3'-OH group in the active sites of natural polymerases (Burgess et al. A Chemistry European Journal, 1999, 5: 951-960). To generally perform the SBS using dNTPs having a 3'-O-blocking group, a suitably modified polymerase having a larger space surrounding the 3'-OH group in its active site is needed. Recently, professor Ju's group at Columbia University performed the SBS using 3'-O-allylated dNTPs and 3'-O-aziomethylated dNTPs (Seo et al. PNAS, 2005, 102: 5926-5931; Guo et al. PNAS, 2008, 105: 9145-9150). To insert such nucleotides having 3'-O-blcking groups, the above group used a modified DNA polymerase obtained from the strain collected from an Eastern Pacific crater (Southworth et al. PNAS, 1996, 93: 5281-5285). This modified DNA polymerase is now commercially available under the brand name of 'Therminator II' provided by New England Biolabs, Inc. Kwiatkowski et al. of Helicos Biosciences Corp. designed 3'-O-hydrocarbyldithiomethyl dNTPs for the SBS (Kwiatkowski et al., 2007, US20077279563), and Parce et al. of Caliper Life Sciences, Inc. used a blocking group containing a phosphate group or a carbamate group (Parce et al., 2006, US20067105300).

If, instead of DRTs, the SBS could utilize mono-modified reversible terminators (MRTs), in which the reversible blocking group on the 3'-OH group played a dual role as a fluorescence-signal reporter as well as a reversible terminator, fluorescent labels on nucleobases would no longer be needed. The MRTs could then be transformed back into the natural state without residual molecular scars after removal of the fluorescent blocking groups from 3'-OH moieties (see FIG. 1, right). However, this principal of sequencing using MRTs and conventional polymerases has not been realized yet.

The present inventors completed the present invention by confirming that the SBS can be successfully carried out by the processes of 1) designing a MRT having a chemical structure playing a role as a blocking group as well as capable of emitting a fluorescence-signal in its 3'-OH group not in its base, and 2) inserting the MRT using conventional polymerases→sequencing by the recognition of fluorescence signal of a 3'-0-fluorescent blocking group→removing the fluorescent blocking group→the second insertion of the MRT (see FIG. 2).

SUMMARY OF THE INVENTION

It is an object of the present invention to provide a mono-modified reversible terminator (MRT) which is a nucleoside triphosphate having a chemically removable reversible blocking group capable of emitting fluorescence signal at its 3'-OH group, and a sequencing method (sequencing-by-synthesis) using the same.

To achieve the above object, the present invention provides a modified nucleoside triphosphate (dNTP) having a reversible fluorescent group removable by physical or chemical reaction at the 3'-OH group of the modified dNTP which has a ribose or a deoxyribose as a sugar backbone.

The present invention also provides a sequencing method using the said nucleotide monomers or their multimers.

In addition, the present invention provides a sequencing kit for sequencing-by-synthesis (SBS) containing the said nucleotide monomers or their multimers.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
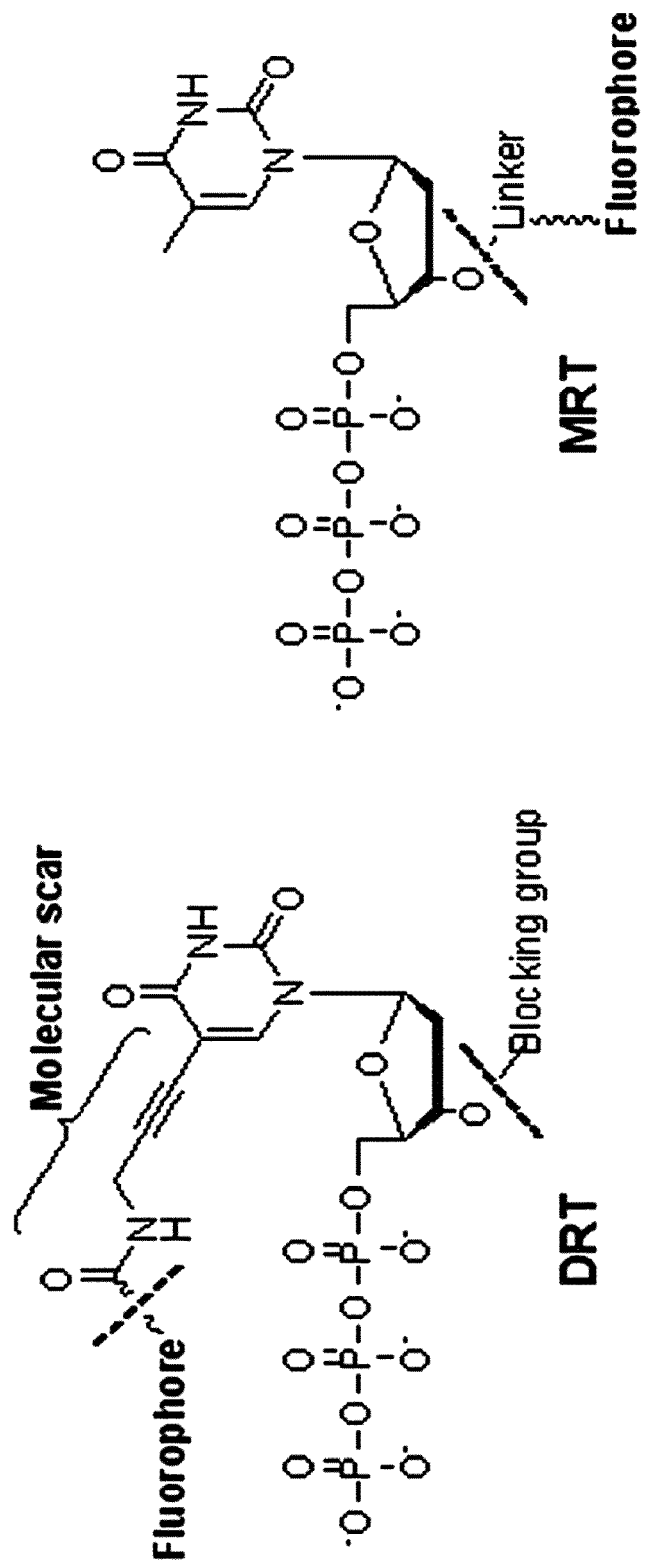
FIG. 1 is a set of diagrams illustrating a dual-modified reversible terminator (DRT) which is a nucleoside triphosphate used for conventional sequencing-by-synthesis (SBS) technologies with a reversible blocking group on the 3'-OH group and a fluorescent group (fluorophore) on nucleobase (left), and a mono-modified reversible terminator (MRT) which is a nucleoside triphosphate used for the SBS of the present invention with a reversible blocking group on the 3'-OH group played a dual role as a fluorescence-signal reporter as well as a reversible terminator.
Figure 2:
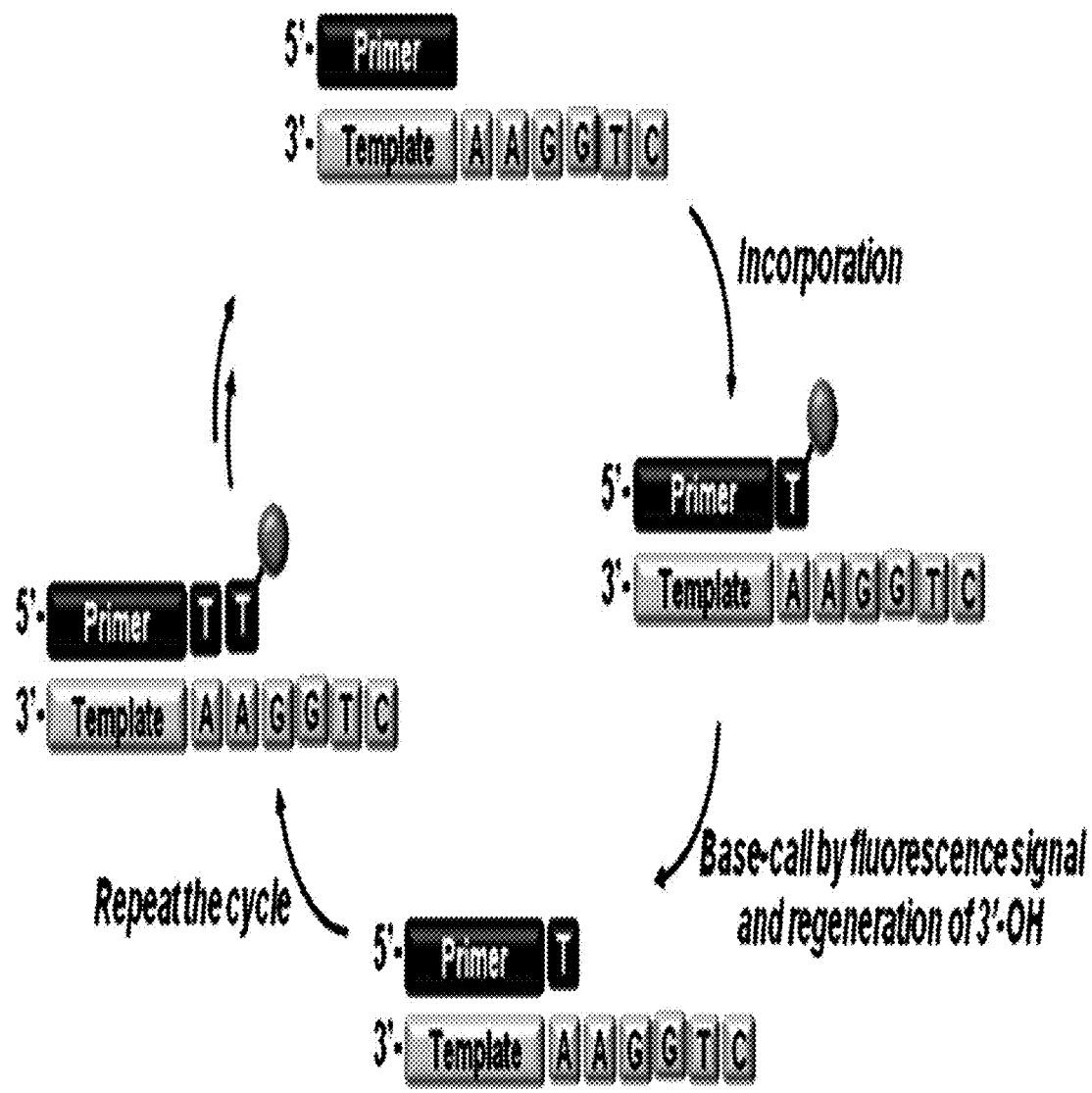
FIG. 2 is a diagram illustrating the processes of sequencing-by-synthesis (SBS) comprising the following steps: inserting a mono-modified reversible terminator (MRT) using a polymerase; sequencing by detecting fluorescence signal from a fluorescent 3'-O-blocking group; and inserting a second MRT.

Hereinafter, the present invention is described in detail.

The present invention provides a novel compound or its salts having the structure of the following [Formula 1]:

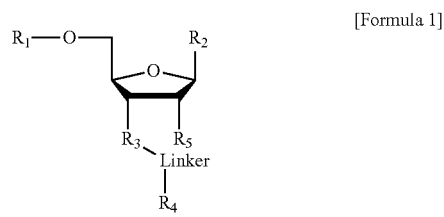

In [Formula 1], $R_1$ is H, a protecting group, a monophosphate, a diphosphate, a triphosphate or a nucleic acid, $R_2$ is a nucleobase, which is a purine, a pyrimidine or a deazapurine, $R_3$ is an electron withdrawing functional group or an electron donating functional group, which is selected from a group consisting of O, N, S, and Si, $R_4$ is a fluorophore that emits fluorescence or phosphorescence at 300-1500 nm, which is exemplified by coumarin, AlexaFluor, Bodipy, fluorescein, tatramethylrhodamine, Cy5, Cy3, Texas Red or its derivatives, $R_5$ is an electron withdrawing functional group or an electron donating functional group, which is selected from a group consisting of O, N, S, and Si, and Linker is a chemical group including C, O, N, S, P or Si, which contains allyl, azidomethyl, 2-nitrobenzyl, ether, amide, ester, phosphodiester, hydroxylamine, oxime carbamate, thioether, sulfoxide, imine, amine, methylene, disulfide, urea or thiourea group.

Not only the novel compound represented by formula 1 but also pharmaceutically acceptable salts, solvates or hydrates and prodrugs prepared from the same are included in the present invention.

The compound of the present invention is preferably a nucleotide monomer having a reversible fluorescent group that is removable by physical or chemical reaction in the 3'-OH moiety of a nucleoside triphosphate having a ribose or a deoxyribose as a sugar backbone, but not always limited thereto.

The said nucleotide monomer preferably has the structure of the following [Formula 2], but not always limited thereto:

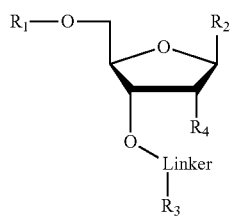

[Formula 2]

In [Formula 2], $R_1$ is triphosphate, $R_2$ is nucleobase, $R_3$ is fluorophore, and $R_4$ is H (hydrogen) or OH (hydroxyl).

The said fluorophore is preferably composed of a fluorophore (FL) alone or a fluorophore and a linker connecting the fluorophore to a 3'-OH group. At this time, the linker is preferably the one that can be cut off by one or more methods selected from the group consisting of a physical method, a chemical method, a physiochemical method, a heating method and an irradiating method to restore a free 3'-OH group, but not always limited thereto.

The fluorescent group conjugated to the 3'-OH group preferably acts as a reversible terminator that allows only one nucleotide to be inserted and then inhibits polymerization and further can be removed to continue the polymerization, and at the same time acts as a fluorescence signal reporter for sequencing, but not always limited thereto.

The fluorophore is preferably selected from the group consisting of coumarin, AlexaFluor, Bodipy, fluorescein, tetramethylrhodamine, Cy5, Cy3, Texas Red and its derivatives, but not always limited thereto.

The linker herein is preferably selected from the group consisting of alkyl, allyl, azidomethyl, disulfide, 2- or 4-nitrobenzyl and a mixture thereof, but not always limited thereto.

In a preferred embodiment of the present invention, said nucleotide monomer is preferably 3'-O-(7-hydroxycoumarin)-deoxythimidine triphosphate, but not always limited thereto.

In the present invention, the compound can be prepared by the following [Reaction Formula 1], but not always limited thereto:

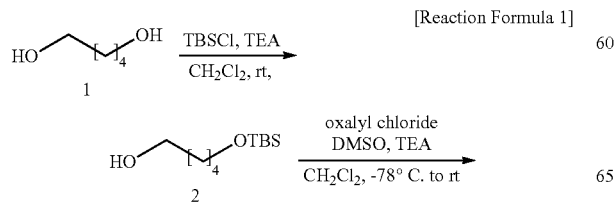

[Reaction Formula 1]

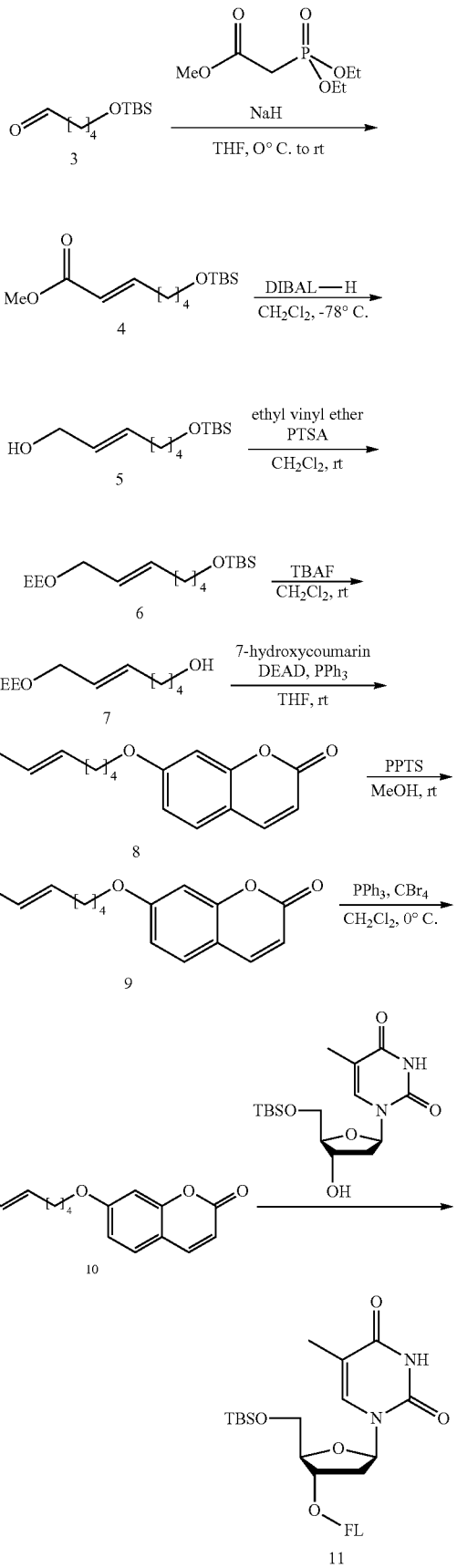

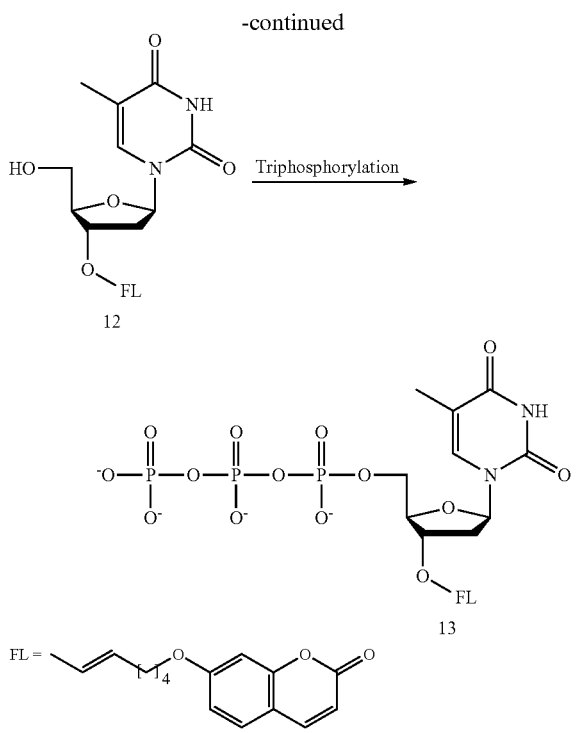

The present invention also provides a DNA sequencing method (sequencing-by-synthesis) using nucleotide monomers or their multimers having a reversible fluorescent group being removed physically or chemically, which is linked to a 3'-OH moiety of a nucleoside triphosphate having a ribose or a deoxyribose as a sugar backbone.

The sequencing method is described as follows: A fluorophore is labeled not to a base but to a 3-OH moiety of a nucleoside triphosphate having a ribose or a deoxyribose as a sugar backbone, and thus during the nucleotide synthesis using polymerase, fluorescence signal of the inserted fluorophore conjugated to the 3'-OH group is detected, leading to sequencing.

Particularly, the sequencing method comprises the following steps, but not always limited thereto:

1) synthesizing a mono-modified reversible terminator (MRT) having a reversible fluorescent blocking group being removed physically or chemically on a 3'-OH moiety of a nucleoside triphosphate having a ribose or a deoxyribose as a sugar backbone;

2) extending a primer by one nucleotide using a nucleotide chain of interest as a template, using the MRT of step 1) and DNA or RNA polymerase;

3) identifying a base of an extended nucleotide chain by detecting fluorescence signal from the reversible fluorescent blocking group conjugated to the 3'-OH group of the extended nucleotide chain resulted from polymerization of step 2);

4) removing the reversible fluorescent blocking group from the extended nucleotide chain of step 3) and then restoring a free 3'-OH group to continue polymerization; and 5) repeating steps from 2) to 4) to determine base sequence of a target template chain.

In the above method, the reversible fluorescent blocking group of step 1) is preferably composed of a fluorophore (FL) and a linker connecting the FL to the 3'-OH group, but not always limited thereto. The linker herein is exemplified by alkyl, allyl, azidomethyl, disulfide, 2- or 4-nitrobenzyl group and a mixture thereof. The Fluorophore is exemplified by coumarin, AlexaFluor, Bodipy, fluorescein, tetramethylrhodamine, Cy5, Cy3, Texas Red and their derivatives. To synthesize dNTP having a fluorescent 3'-O-blocking group, the conventional synthesis method for other 3'-O-blocking groups are used but only modified, precisely the reversible fluorescent blocking group is used instead of other blocking groups.

In the above method, the nucleotide chain of interest of step 2) is preferably DNA that can be a target of sequencing. At this time, the DNA is preferably a genomic DNA, a plasmid, or an oligonucleotide, but not always limited thereto. The DNA polymerase includes any polymerases that can accept the MRT of step 1) as a substrate, which can be selected among thermophilic or mesophilic polymerases or their mutants, but not always limited thereto.

The template prepared for polymerization reaction and a double stranded DNA formed by the primer and the template can be supported on a solid phase. A MRT is inserted into 3'-end of the primer by the polymerase, and then the polymerization is terminated by the action of the reversible fluorescent 3'-O-blocking group of the MRT. Then, excessive MRTs not participated in the polymerization and other byproducts are washed out.

In the above method, the identification of the base of step 3) can be performed by detecting fluorescence emitted from the reversible fluorescent 3'-O-blocking group of the MRT inserted in the 3'-end of the primer of step 2). The detection of fluorescence is performed by observing the solid phase on which the template and the double stranded DNA are supported under fluorescent microscope. Or the fluorescence of solution containing such double stranded DNAs is measured by fluorescence detector, but not always limited thereto.

In the above method, the elimination of step 4) preferably comprising removing the reversible fluorescent blocking group containing a fluorophore to be detected via a chemical or a enzymatic method, but not always limited thereto. Provided that the linker of said reversible fluorescent blocking group is allyl, Pd catalyst can be used for the chemical reaction to remove the reversible fluorescent blocking group. Provided that the linker is azidomethyl, tris-alkylphosphine or tris-arylphosphine or their derivatives can be used to remove the reversible fluorescent blocking group. In the case that the linker is disulfide, β-mercaptoethanol or dithiothreitol (DTT) can be used to remove the fluorescent blocking group. If the linker is nitrobenzyl, UV (300-400 nm) is irradiated to remove the reversible fluorescent blocking group.

Once the reversible fluorescent blocking group is removed by one of the above methods, the 3'-OH group is restored so that a complementary MRT can be inserted in the next base of the template. So, the processes from step 1) to step 4) can be repeated. That is, along with the polymerization, each base of the template can be analyzed one by one, which leads to sequencing-by-synthesis (SBS).

The sequencing method of the present invention using MRT for the SBS has two significant effects which are better than the conventional SBS using DRT. First, according to the sequencing method of the present invention, a base is not labeled with fluorescence, so that there is no molecular scar remaining after the elimination of a fluorescent blocking group upon completion of fluorescence analysis, which brings higher efficiency for continuous polymerization. Second, according to the sequencing method of the present invention, the fluorescent blocking group is conjugated to a 3'-OH group. That is, the MRT is supposed to remove only one marker. So, compared with the conventional method in which all of fluorescence-label of base and 3'-O-blocking group are supposed to be removed, the method of the present invention gives significantly higher yield.

Therefore, SBS using the MRT of the present invention facilitates efficient sequencing of longer chain because it is more efficient and thus gives a higher yield in each reaction cycle than the conventional methods.

In a preferred embodiment of the present invention, to investigate whether the primer could be extended by using the MRT, 3'-O-(7-hydroxycoumarin)-dTTP (MRT, compound 13) and biotin labeled primer were polymerized. Then, molecular weight was analyzed by using MALDI-TOF mass spectrometry. As a result, the primer extension by 3'-O-(7-hydroxycoumarin)-dTTP was confirmed (see FIG. 3).

In another preferred embodiment of the present invention, it was investigated whether the base inserted in a primer by polymerase could be analyzed using fluorescence-labeled MRT. Polymerization was performed by the same manner as described above and the obtained DNA immobilized on magnetic beads was eluted with biotin solution. Then, the fluorescence intensity of the DNA was measured using a fluorescence spectrometer. As a result, it was confirmed that the fluorescence signal of the extended primer was increased, compared with the fluorescence signal from the primer before extension (see FIG. 4).

In another preferred embodiment of the present invention, it was investigated whether the fluorescence label of the MRT could be successfully removed after primer extension. Polymerization was performed by the same manner as described above and then the extended primer having a free 3'-OH was obtained from the DNA immobilized on magnetic beads. Mass analysis was performed using MALDI-TOF mass spectrometry. As a result, fluorescence label of the MRT could be successfully removed after primer extension (see FIG. 3).

In another preferred embodiment of the present invention, it was investigated whether the next primer chain could be extended by another MRTs after the elimination of the fluorescence label. Fluorescent group of the 3'-end was removed by the same manner as described above and then the obtained DNA was purified by reverse-phased HPLC. Second extension with the MRT was performed using the obtained DNA as a primer, followed by mass analysis using MALDI-TOF mass spectrometry. As a result, it was confirmed that the primer could be extended by the MRT having a 3'-O-fluorescence label and the primer could also be extended by another MRTs after the analysis and the elimination of the fluorescence label (see FIG. 3).

Therefore, it was confirmed that sequencing-by synthesis could be successfully carried out by analyzing fluorescence signal of each extension step using MRT of the present invention.

The present invention also provides a sequencing kit for sequencing-by-synthesis (SBS) containing nucleotide monomers or their multimers having a physically or a chemically removable reversible fluorescent group on its 3'-OH moiety of a nucleoside triphosphate having a ribose or a deoxyribose as a sugar backbone.

In addition, the present invention provides a use of the sequencing kit for sequencing-by-synthesis (SBS) containing nucleotide monomers or their multimers having a physically or a chemically removable reversible fluorescent group on its 3'-OH moiety of a nucleoside triphosphate having a ribose or a deoxyribose as a sugar backbone.

The nucleotide monomer of the present invention can not only terminate the extension of nucleotide chain but also detect fluorescence signal from its 3'-OH to identify the base inserted. As well, upon completion of the fluorescence signal analysis, the blocking group attached to the 3'-OH group can be effectively removed and thereby a free 3'-OH functional group can be restored, which makes a next monomer be inserted, suggesting that continuous sequencing is possible. Therefore, it can be effectively used as a component for the sequencing kit.

ADVANTAGEOUS EFFECTIVENESS

The sequencing method (sequencing-by-synthesis) of the present invention using a mono-modified reversible terminator (MRT) is advantageous as follows: First, according to the method of the present invention, a base is not labeled with fluorescence, so that there is no molecular scar remaining after the elimination of the fluorescent blocking group upon completion of fluorescence analysis, which brings higher efficiency for continuous polymerization. Second, according to the method of the present invention, the fluorescent blocking group is conjugated to a 3'-OH group reversible. Thus, compared with the conventional method in which all of fluorescence-label of base and 3'-O-blocking group are supposed to be removed, the method of the present invention gives significantly higher yield.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

EXAMPLE 1

Synthesis of 3'-O-(7-hydroxycoumarin)-dTTP, the Mono-Modified Reversible Terminator (MRT)

<1-1> Synthesis of Compound 2

To a solution of 1,5-pentanediol (66.9 mmol) and tert-butyldimethylsilyl chloride (TBSCl, 66.9 mmol) in dichloromethane (100 mL) was added triethylamine (100.4 mmol). The reaction mixture was stirred for 5 min at room temperature. The reaction mixture was diluted with dichloromethane, washed with water, dried over anhydrous $MgSO_4$, and concentrated using rotary evaporator. The residue was purified by column chromatography (silica gel, hexane/ethyl acetate=10/1) to give the target compound as a colorless oil (95% yield).

The obtained compound was analyzed by NMR and the results are as follows: $^1$H NMR (300 MHz, $CDCl_3$) d 3.63-3.58 (m, 4H), 1.59-1.49 (m, 4H), 1.41-1.35 (m, 2H), 0.87 (s, 9H), 0.03 (s, 6H) ppm; $^{13}$C NMR (75 MHz, $CDCl_3$) δ 63.4, 62.7, 32.7, 32.6, 26.2, 22.2, 18.6, −5.1 ppm; IR(KBr) 3348, 2932, 2859, 1472, 1389, 1362, 1255, 1102, 1006, 939, 836, 775 $cm^{-1}$; HRMS(DART) calcd for $[C_{11}H_{27}O_2Si]^+$: 219.1775, found: 219.1771.

<1-2> Synthesis of Compound 3

To a solution of oxalyl chloride (1.5 mmol) in dichloromethane (70 mL) was added DMSO (65.5 mmol). The mixture was stirred for 15 min at −78° C. To the above reaction mixture was added the compound 2 dissolved in dichloromethane (50 mL). The reaction mixture was then stirred for another 15 min. Finally, to the reaction mixture was added triethylamine (297.8 mmol), and the temperature was slowly increased to room temperature for 30 min with stirring. The reaction mixture was diluted with dichloromethane, washed with water, dried over anhydrous $MgSO_4$, and concentrated using rotary evaporator. The residue was purified by column chromatography (silica gel, hexane/ethyl acetate=30:1) to give the target compound as a pale yellow oil (96% yield).

The obtained compound was analyzed by NMR and the results are as follows: $^1$H NMR (300 MHz, CDCl$_3$) δ 9.76 (s, 1H), 3.62-3.58 (t, J=6.3 Hz, 2H), 2.46-2.41 (t, J=7.2 Hz, 2H), 1.73-1.48 (m, 4H), 0.87 (s, 9H), 0.03 (s, 6H) ppm; $^{13}$C NMR (75 MHz, CDCl$_3$) δ 62.7, 43.8, 32.3, 26.1, 18.8, 18.5, −5.2 ppm; IR(KBr) 3398, 2922, 2852, 1736, 1650, 1466, 1260, 1026, 802 cm$^{-1}$; HRMS(DART) calcd for [C$_{11}$H$_{25}$O$_2$Si]$^+$: 217.1618, found: 217.1619.

<1-3> Synthesis of Compound 4

To a suspension of NaH (60% dispersion in mineral oil, 22.3 mmol) in THF (30 mL) was dropwisely added diethylphosphonoacetate (22.3 mmol) at 0° C. To this reaction mixture was added the compound 3 dissolved in THF (30 mL). The reaction mixture was stirred at room temperature for 2 h. The reaction was quenched with saturated NH$_4$Cl solution. The solvent was removed by evaporation, and the residue was diluted with ethyl acetate, washed with brine, and dried over anhydrous MgSO$_4$, and concentrated using rotary evaporator. The residue was purified by column chromatography (silica gel, hexane/ethyl acetate=30:1) to give the target compound as a colorless oil (78% yield).

The obtained compound was analyzed by NMR and the results are as follows: $^1$H NMR (300 MHz, CDCl3) δ 7.00-6.90 (m, 1H), 5.84-5.77 (m, 1H), 3.70 (s, 3H), 3.61-3.57 (t, J=6.3 Hz, 2H), 2.21-2.19 (m, 2H), 1.53-1.49 (m, 4H), 0.87 (s, 9H), 0.03 (s, 6H) ppm; $^{13}$C NMR (75 MHz, CDCl3) δ 167.1, 149.5, 121.2, 62.8, 51.4, 32.4, 32.1, 26.1, 24.6, 18.5, −5.2 ppm; IR(KBr) 2932, 2858, 1729, 1658, 1471, 1437, 1257, 1101, 1039, 837, 776 cm−1; HRMS(DART) calcd for [C14H29O3Si]$^+$: 273.1880, found: 273.1875.

<1-4> Synthesis of Compound 5

To a solution of the compound 4 (10.7 mmol) dissolved in dichloromethane (50 mL) was dropwisely added DIBAL-H (1.0 M in toluene, 12.8 mmol) at −78° C., and the mixture was stirred at −78° C. for 2 h. The reaction mixture was allowed to slowly warm up to 0° C. The reaction was quenched with saturated NH$_4$Cl solution, then filtered through Celite. The filtrate was diluted with dichloromethane, washed with brine, dried over anhydrous MgSO$_4$, and concentrated using rotary evaporator. The residue was purified by column chromatography (silica gel, hexane/ethyl acetate=10:1) to give the target compound as a colorless oil (77% yield).

The obtained compound was analyzed by NMR and the results are as follows: $^1$H NMR (300 MHz, CDCl$_3$) δ 5.71-5.57 (m, 2H), 4.07-4.06 (d, J=5.1 Hz, 2H), 3.61-3.56 (t, J=6.3 Hz, 2H), 2.08-2.01 (m, 2H), 1.53-1.37 (m, 4H), 0.87 (s, 9H), 0.03 (s, 6H) ppm; $^{13}$C NMR (75 MHz, CDCl$_3$) δ 133.0, 129.5, 63.6, 63.3, 32.5, 32.2, 26.2, 25.6, 18.6, −5.1 ppm; IR(KBr) 3364, 2930, 2858, 1470, 1254, 1101, 1006, 836, 775 cm$^{-1}$; HRMS(DART) calcd for [C$_{13}$H$_{29}$O$_2$Si]$^+$: 245.1931, found: 245.1932.

<1-5> Synthesis of Compound 6

To a solution of the compound 5 (7.55 mmol) dissolved in dichloromethane (50 mL) was added pyridinium p-toluenesulfonate (0.76 mmol) and ethyl vinyl ether (37.76 mmol) at 0° C. The reaction mixture was stirred at room temperature for 19 h. After the solvent was evaporated, the residue was diluted with dichloromethane, washed with brine, dried over anhydrous MgSO$_4$, and concentrated using rotary evaporator. The residue was purified by column chromatography (silica gel, hexane/ethyl acetate=30:1) to give the target compound as a colorless oil (86% yield).

The obtained compound was analyzed by NMR and the results are as follows: $^1$H NMR (300 MHz, CDCl$_3$) δ 5.73-5.49 (m, 2H), 4.73-4.68 (q, J=10.5 Hz, 1H), 4.06-3.88 (m, 2H), 3.67-3.56 (m, 3H), 3.52-3.41 (m, 1H), 2.07-2.00 (q, J=14.1 Hz, 2H), 1.55-1.35 (m, 4H), 1.30-1.29 (d, J=5.4 Hz, 3H), 1.21-1.16 (t, J=7.2 Hz, 3H), 0.87 (s, 9H), 0.02 (s, 6H) ppm; $^{13}$C NMR (75 MHz, CDCl$_3$) δ 134.2, 126.7, 99.0, 66.1, 63.1, 60.5, 32.5, 32.2, 26.1, 25.520.1, 18.5, 15.5, −5.1 ppm; IR(KBr) 2932, 2859, 1471, 1387, 1339, 1254, 1060, 1032, 971, 837, 776 cm$^{-1}$ <1-6> Synthesis of Compound 7

To a solution of the compound 6 (6.28 mmol) dissolved in THF (50 mL) was added tetrabutylammonium fluoride (1.0 M in THF, 9.42 mL, 9.42 mmol) at room temperature, and the mixture was stirred for 15 h. After the solvent was evaporated, the residue was diluted with dichloromethane, washed with brine, dried over anhydrous MgSO$_4$, and concentrated using rotary evaporator. The residue was purified by column chromatography (silica gel, hexane/ethyl acetate=2:1) to give the target compound as a colorless oil (90% yield).

The obtained compound was analyzed by NMR and the results are as follows: $^1$H NMR (300 MHz, CDCl$_3$) δ 5.73-5.50 (m, 2H), 4.73-4.68 (q, J=10.5 Hz, 1H), 4.06-3.88 (m, 2H), 3.66-3.56 (m, 3H), 3.52-3.41 (m, 1H), 2.10, 2.03 (q, J=14.4 Hz, 2H), 1.59-1.41 (m, 4H), 1.31-1.28 (d, J=5.1 Hz, 3H), 1.21-1.16 (t, J=7.5 Hz, 3H) ppm; $^{13}$C NMR (75 MHz, CDCl$_3$) δ 134.2, 133.2, 126.9, 99.2, 66.2, 62.9, 60.7, 32.5, 32.2, 25.4, 20.1, 15.6 ppm; IR(KBr) 9419, 2979, 2933, 2887, 1670, 1445, 1381, 1340, 1131, 1090, 1058, 1031, 972, 870 cm$^{-1}$; HRMS(DART) calcd for [C$_{11}$H$_{23}$O$_3$]$^+$: 203.1642, found: 203.1639.

<1-7> Synthesis of Compound 8

To a solution of the compound 7 (2.21 mmol), triphenylphophine (5.21 mmol) and 7-hydroxycoumarin (2.23 mmol) in THF (5 mL) was added azodicarboxylic acid diethyl ester (2.2 M in toluene, 2.9 mL, 6.37 mmol) at 0° C. The reaction mixture was stirred at room temperature for 12 h. The solvent was removed by evaporation, and the residue was diluted with dichloromethane, washed with brine, dried over anhydrous MgSO$_4$, and concentrated using rotary evaporator. The residue was purified by column chromatography (silica gel, hexane/ethyl acetate=10:1) to give the target compound as a colorless oil (77% yield).

The obtained compound was analyzed by NMR and the results are as follows: $^1$H NMR (300 MHz, CDCl$_3$) δ 7.62-7.59 (d, J=9.3 Hz, 1H), 7.35-7.32 (d, 8.4 Hz, 1H), 6.82-6.77 (m, 2H), 6.24-6.20 (d, J=10.5 Hz, 1H), 5.75-5.53 (m, 2H), 4.73-4.65 (m, 1H), 4.07-3.89 (m, 4H), 3.66-3.42 (m, 2H), 2.15-2.08 (q, J=14.1 Hz, 2H), 1.85-1.76 (m, 2H), 1.61-1.51 (m, 2H), 1.31-1.29 (d, J=5.1 Hz, 3H), 1.21-1.16 (t, J=7.5 Hz, 3H) ppm; $^{13}$C NMR (75 MHz, CDCl$_3$) δ 162.5, 161.2, 156.0, 143.7, 133.5, 129.0, 127.2, 113.0 (x 2), 112.6, 101.4, 99.1, 68.5, 66.1, 60.7, 32.1, 28.6, 25.6, 20.1, 15.5 ppm.

<1-8> Synthesis of Compound 9

To a solution of the compound 8 (3.14 mmol) dissolved in methanol (30 mL) was added pyridinium p-toluenesulfonate (1.57 mmol) at 0° C. The reaction mixture was stirred at room temperature for 3 h. The solvent was evaporated, and the residue was diluted with dichloromethane, washed with brine, dried over anhydrous MgSO$_4$, and concentrated using rotary evaporator. The residue was purified by column chromatography (silica gel, hexane/ethyl acetate=2:1) to give the target compound as a colorless solid (95% yield).

The obtained compound was analyzed by NMR and the results are as follows: $^1$H NMR (300 MHz, CDCl$_3$) δ 7.62-7.59 (d, J=9.6 Hz, 1H), 7.35-7.32 (d, J=8.7 Hz, 1H), 6.82-6.77 (m, 2H), 6.24-6.20 (dd, J=9.0 Hz, 2.1 Hz, 1H), 5.69-5.65 (m, 2H), 4.09 (s, 2H), 4.02-3.97 (m, 2H), 2.15-2.09 (q, J=12.6 Hz, 2H), 1.86-1.76 (m, 2H), 1.61-1.51 (m, 2H) ppm; $^{13}$C NMR (75 MHz, CDCl$_3$) δ 162.5, 161.7, 156.0, 144.0, 132.0, 130.0, 129.1, 113.1, 112.9, 112.6, 101.4, 68.6, 63.5, 32.0, 28.6, 25.6 ppm; IR(KBr) 3435, 2953, 1731, 1614, 1555, 1508, 1402, 1351, 1282, 1232, 1201, 1232, 1201, 1127, 997, 836 cm$^{-1}$; m.p.=70° C.; HRMS(DART) calcd for [C$_{16}$H$_{19}$O$_4$]$^+$: 275.1278, found: 275.1277.

<1-9> Synthesis of Compound 10

To a solution of the compound 9 (2.80 mmol) and triphenylphosphine (5.60 mmol) in dichloromethane (15 mL) was added carbon tetrabromide (5.89 mmol) at 0° C. The reaction mixture was stirred for 1 h. The reaction was quenched with saturated NaHCO$_3$ solution. The mixture was diluted with dichloromethane, washed with brine, dried over anhydrous MgSO$_4$, and concentrated using rotary evaporator. The residue was purified by column chromatography (silica gel, hexane/ethyl acetate=30:1) to give the target compound as a yellow oil (63% yield).

The obtained compound was analyzed by NMR and the results are as follows: $^1$H NMR (300 MHz, CDCl$_3$) δ 7.63-7.60 (d, J=9.6 Hz, 1H), 7.36-7.33 (d, J=8.7 Hz, 1H), 6.83-6.77 (m, 2H), 6.25-6.21 (d, J=9.9 Hz, 1H), 5.82-5.66 (m, 2H), 4.02-3.93 (m, 4H), 2.18-2.11 (q, J=13.5 Hz, 2H), 1.86-1.76 (m, 2H), 1.62-1.54 (m, 2H) ppm; $^{13}$C NMR (75 MHz, CDCl$_3$) δ 162.5, 161.4, 156.1, 143.8, 136.0, 129.1, 127.2, 113.1(x 2), 112.7, 101.5, 68.5, 33.7, 31.9, 28.6, 25.4 ppm; IR(KBr) 2938, 1733, 1614, 1555, 1508, 1401, 1350, 1281, 1231, 1201, 1123, 969, 892, 835 cm$^{-1}$; m.p=88-90° C.; HRMS(DART) calcd for [C$_{16}$H$_{18}$BrO$_3$]$^+$: 337.0434, found: 337.0432.

<1-10> Synthesis of Compound 11

To a suspension of NaH (60% dispersion in mineral oil, 4.93 mmol) in THF (10 mL) was added 5'-O-tert-butyldimethylsilylthymidine (2.46 mmol) at 0° C. To this mixture was added compound 10, and the reaction mixture was stirred at room temperature for 48 h. The reaction was quenched with saturated NH$_4$Cl solution at 0° C. The solvent was evaporated, and the residue was diluted with dichloromethane, washed with brine, dried over anhydrous MgSO$_4$, and concentrated using rotary evaporator. The residue was purified by column chromatography (silica gel, dichloromethane/methanol=50:1) to give the target compound as a white foam (62% yield).

The obtained compound was analyzed by NMR and the results are as follows: $^1$H NMR (300 MHz, CDCl$_3$) δ 8.36 (s, 1H), 7.63-7.60 (d, J=9.3 Hz, 1H), 7.48 (s, 1H), 7.36-7.33 (d, J=8.7 Hz, 1H), 6.82-6.74 (m, 2H), 6.30-6.25 (m, 1H), 6.24-6.21 (d, J=9.6 Hz, 1H), 5.76-5.51 (m, 2H), 4.09-3.73 (m, 8H), 2.43-2.37 (m, 1H), 2.16-2.09 (q, J=14.1 Hz, 2H), 1.97-1.77 (m, 3H), 1.89 (s, 3H), 1.62-1.52 (m, 2H) ppm; $^{13}$C NMR (75 MHz, CDCl$_3$) δ 164.5, 162.5, 161.5, 156.1, 150.8, 143.8, 135.7, 134.5, 129.1, 126.6, 113.1, 112.6, 111.0, 101.5, 85.4, 85.3, 78.9, 70.1, 68.6, 63.9, 38.2, 32.1, 31.2, 28.7, 36.1, 25.6, 18.6, 12.8, −5.1 ppm; IR(KBr) 2924, 2854, 1732, 1614, 1464, 1378, 1279, 1126, 837 cm$^{-1}$; HRMS(DART) calcd for [C$_{32}$H$_{45}$N$_2$O$_8$Si]$^+$: 613.2940, found: 613.2948.

<1-11> Synthesis of Compound 12

To a solution of the compound 11 (0.90 mmol) dissolved in THF (10 mL) was added tetrabutylammonium fluoride (1.0 M in THF 2.64 mL, 2.64 mmol) at room temperature. The reaction mixture was stirred at room temperature for 15 h. The solvent was evaporated, and the residue was diluted with dichloromethane, washed with brine, dried over anhydrous MgSO$_4$, and concentrated using rotary evaporator. The residue was purified by column chromatography (silica gel, dichloromethane/methanol=40:1) to give the target compound as a white solid (87% yield).

The obtained compound was analyzed by NMR and the results are as follows: $^1$H NMR (300 MHz, CDCl$_3$) δ 7.63-7.60 (d, J=9.6 Hz, 1H), 7.37 (s, 1H), 7.36-7.33 (d, J=8.7 Hz, 1H), 6.82-6.76 (m, 2H), 6.24-6.20 (d, J=9.6 Hz, 1H), 6.11-6.07 (t, J=7.5 Hz, 1H), 5.76-5.51 (m, 2H), 4.22-4.20 (m, 1H), 4.08-3.89 (m, 6H), 3.79-3.72 (m, 1H), 2.34-2.29 (m, 2H), 2.16-2.12 (m, 2H), 1.88 (s, 3H), 1.83-1.76 (m, 2H), 1.62-1.57 (m, 2H) ppm; $^{13}$C NMR (75 MHz, CDCl$_3$) δ 164.6, 162.6, 161.8, 156.0, 150.9, 144.1, 137.3, 134.5, 129.2, 126.6, 113.3, 112.7, 111.1, 101.6, 86.7, 85.5, 78.7, 70.4, 68.6, 62.8, 37.7, 32.1, 28.7, 25.5, 20.4, 12.8 ppm; IR(KBr) 2930, 1705, 1613, 1556, 1508, 1470, 1404, 1352, 1280, 1232, 1200, 1130, 1060, 837, 756 cm$^{-1}$; HRMS(DART) calcd for [C$_{26}$H$_{31}$N$_2$O$_8$]$^+$: 499.2075, found: 499.2086.

<1-12> Synthesis of Compound 13

The compound 12 (0.28 mmol) was dissolved in anhydrous pyridine and vacuum-concentrated. It was diluted with anhydrous pyridine (0.28 mL) and anhydrous 1,4-dioxane (0.84 mL) under Ar. To this solution was added 2-chloro-4H-1,3,2-benzodioxaphosphorin-4-one (0.45 mmol) in anhydrous 1,4-dioxane (0.3 mL) and stirred at room temperature for 10 min. To this reaction mixture was added bis(tributylammonium)pyrophosphate (0.33 mmol) and tributylamine (1.10 mmol) in anhydrous DMF (0.80 mL), and the reaction mixture was stirred at room temperature for another 10 minutes. To the reaction mixture was added 1% iodine solution (pyridine/water=98/2, v/v, 5.6 mL) and stirred at room temperature for 15 min. The reaction was quenched with 5% aqueous Na$_2$SO$_3$ solution, and 1M triethylammonium bicarbonate (TEAB) buffer (3 mL) was added. The solution was vacuum-concentrated, redissolved in water (2 mL), and purified by HPLC.

The obtained compound was analyzed by NMR and the results are as follows: $^1$H NMR (300 MHz, CDCl$_3$) δ 7.88-7.85 (d, J=9.3 Hz, 1H), 7.54 (s, 1H), 7.49-7.46 (d, J=7.8 Hz, 1H), 6.23-6.20 (d, J=9.6 Hz, 1H), 6.11-6.06 (m, 1H), 5.82-5.74 (m, 1H), 5.66-5.55 (m, 1H), 4.32 (s, 1H), 4.14-3.92 (m, 7H), 2.33-2.28 (m, 1H), 2.23-2.05 (m, 3H), 1.81-1.71 (m, 2H), 1.76 (s, 3H), 1.54-1.49 (m, 2H) ppm; $^{31}$P NMR (121.4 MHz, D$_2$O) δ −11.55 (s, 1P), −14.00 (d, J=20.8 Hz, 1P), −25.39 (s, 1P) ppm; MALDI-TOF MS [M-H]$^-$: 737.4711.

EXAMPLE 2

Extension of DNA Primer with MRT

The polymerase extension reaction by polymerase was performed in 20 mL of reaction mixture containing 5 mM of a biotinylated primer (5'-biotin-GCTACGACTCACTATG-GACG-3', SEQ. ID. NO: 1), 5 mM of the template (5'-CGTC-CATAGTGAGTCGTAGC-3', SEQ. ID. NO: 2, a complementary base to an inserted base is underlined and bolded), 200 mM of 3'-O-(7-hydroxycoumarin)-dTTP (MRT, compound 13), 1× ThermoPol II reaction buffer (20 mM Tris-HCl/10 mM (NH$_4$)$_2$SO$_4$/10 mM KCl/2 mM MnCl$_2$/0.1% Triton X-100, pH 8.8, New England Biolabs, Inc.), and 4 units of Therminator II DNA polymerase. The reaction was consisted of 20 cycles at 94° C. for 20 sec, 46° C. for 40 sec, and 60° C. for 90 sec. After the reaction, the mixture was incubated with strepatavidin-coated magnetic beads (100 mg, Dynabead MyOne, Invitrogen) in PBS buffer (200 mL) at room temperature for 30 min. The DNA immobilized on beads were then washed twice with 200 mL deionized water and eluted with 40 mL biotin solution (1 mM in deionized water/DMSO=98/2). The eluted DNA was desalted using ZipTip c18 and analyzed by MALDI-TOF MS.

As a result, as shown in FIG. 3b, the primer disappeared by polymerase and molecular weight 7079 peak newly generated by the reaction of the primer and one molecule of 3'-O-

Figure 3:
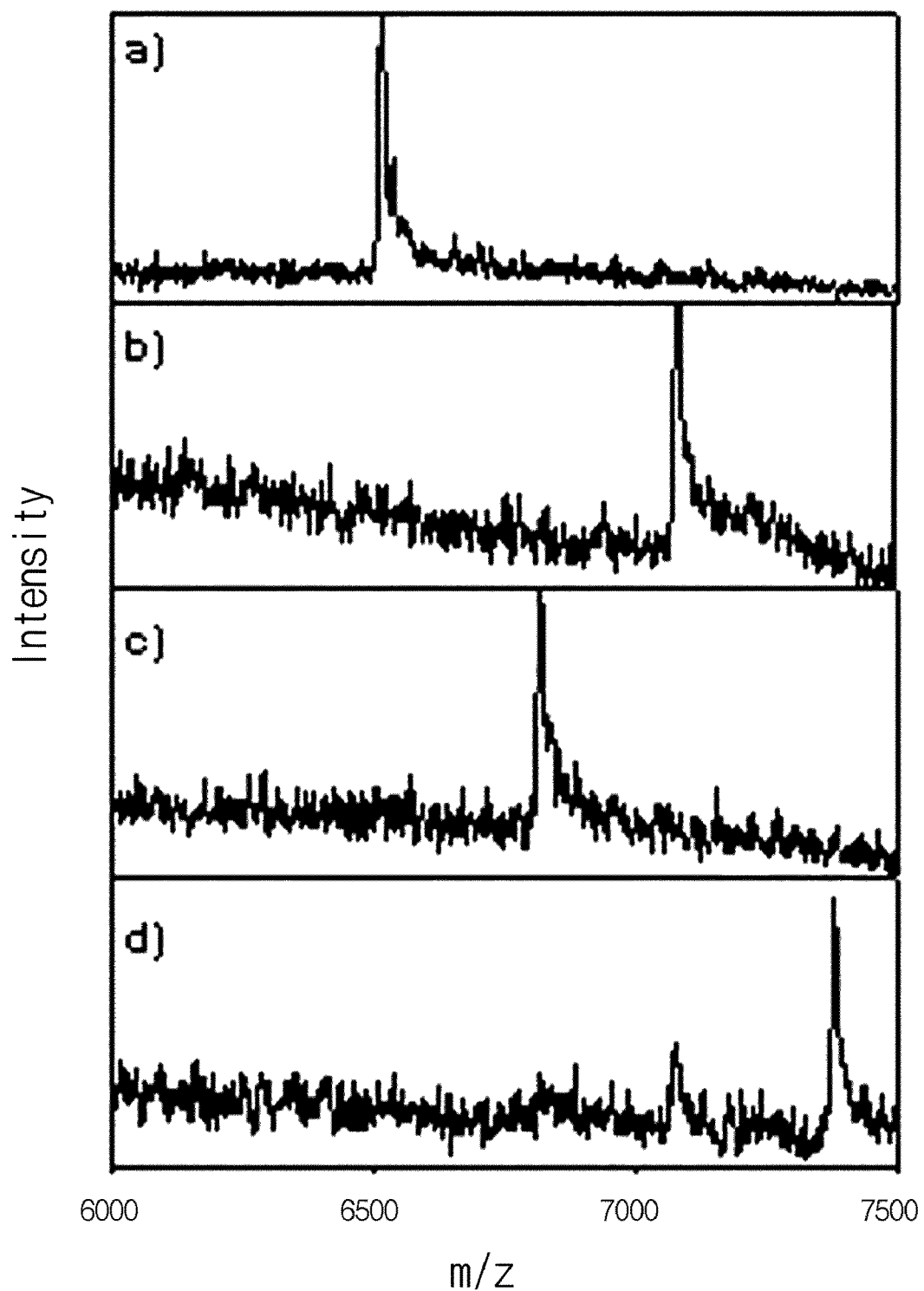
FIG. 3 is a set of diagrams illustrating MALDI-TOF MS spectrum of a primer before the reaction with polymerase and MRT (a); MALDI-TOF MS spectrum of a primer having MRT extended by polymerase (b); MALDI-TOF MS spectrum of a primer having extended MRT after removing a fluorescent blocking group from 3'-end (c); and MALDI-TOF MS spectrum of a primer having a secondarily extended MRT by polymerase after removing the fluorescent blocking group (blue circle: the fluorescent blocking group at 3'-end).

(7-hydroxycoumarin)-dTTP was confirmed. The peak demonstrated increased molecular weight (increased 563 from the primer confirmed in FIG. 3a), which was equal to the molecular weight of the primer chain extended by compound 13 (MRT), indicating that the primer was extended by MRT (FIG. 3).

EXAMPLE 3

Sequencing of Inserted Base Sequence Using 3'-End Fluorescence Label

The DNA immobilized on magnetic beads obtained in Example 2 was eluted with 40 mL biotin solution (1 mM in deionized water/DMSO=98/2), and diluted with 360 mL Tris-HCl buffer (50 mM, pH=8.0). The fluorescence intensity of the solution was measured using LB50B luminescence spectrometer (Perkin-Elmer, Waltham, USA) (excitation at 316 nm). For the control, fluorescence intensity of the reaction mixture without Terminator II DNA polymerase was measured using the same manner as described in Example 2.

Figure 4:
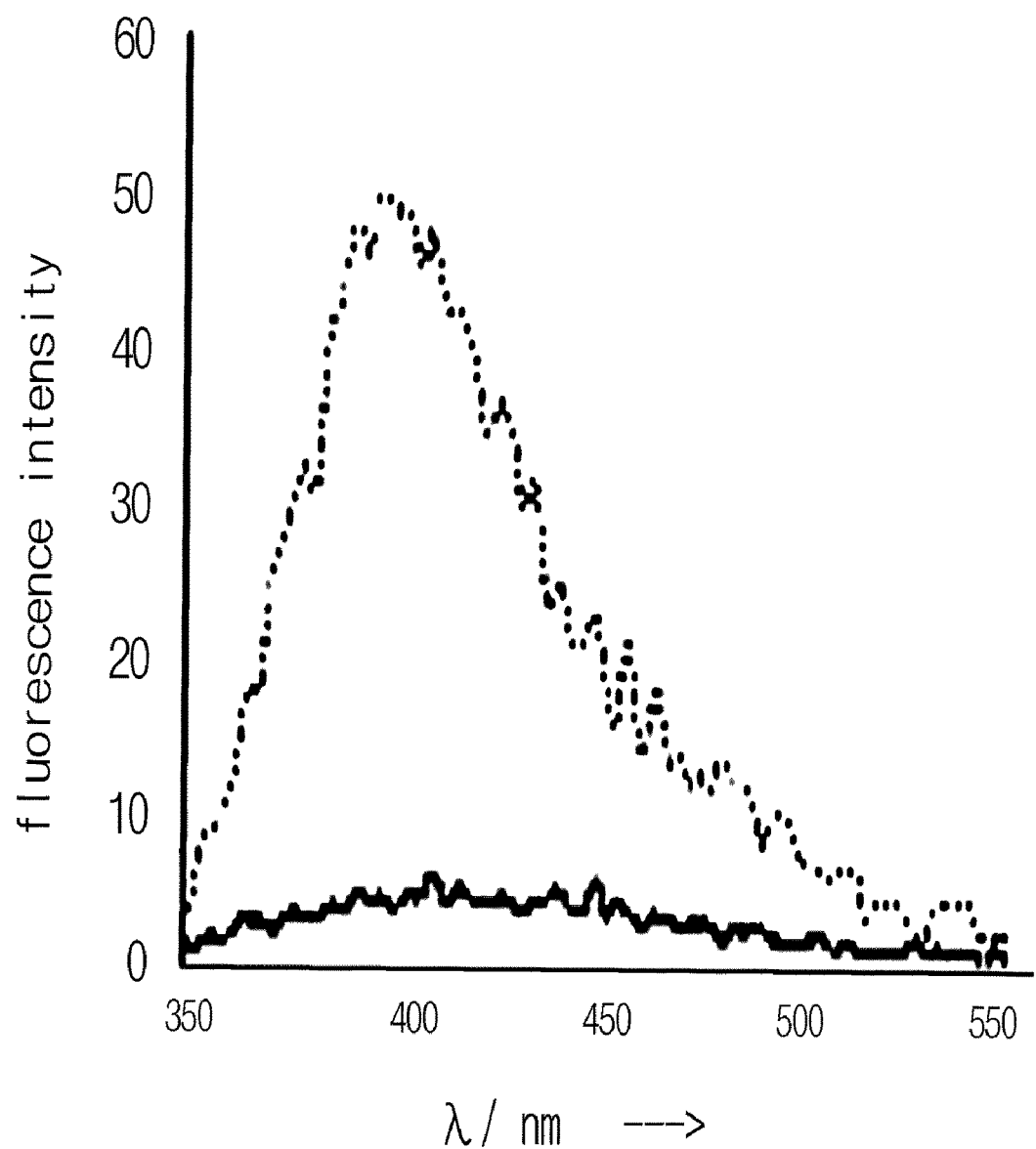
FIG. 4 is a graph illustrating the result of fluorescence intensity measurement before (dotted line) and after (solid line) MRT extension in a primer by polymerase.

As a result, as shown in FIG. 4, the fluorescence signal (dotted line) of the extended primer emitted from the fluorescent group conjugated to the MRT after polymerization with the MRT increased, compared with that of the primer before the reaction (FIG. 4). The above result indicates that the MRT linked fluorescence label can be used for sequencing of bases inserted in the primer by polymerase.

EXAMPLE 4

Elimination of Fluorescence Label Conjugated to the Extended Primer Having MRT at 3'-End and Recovery of 3'-OH Thereby The DNA immobilized on magnetic beads by the same manner as described in Example 2 was incubated at 70° C. for 20 min with the cleavage solution (1 mM biotin, 1.2 mM $Na_2PdCl_4$ TPPTS 9.8 mM), which previously prepared with degassed $H_2O$ (20 mL) to yield the single nucleotide-extended product with free 3'-OH. The supernatant containing the DNA was desalted using ZipTip C18 and analyzed by MALDI-TOF MS.

As a result, as shown in FIG. 3c, the MRT was removed from the reaction product produced from 3'-O-(7-hydroxycoumarin)-dTTP and thus molecular weight 6818 peak, the molecular weight of the extended primer having free, recovered 3'-OH was confirmed (FIG. 3). This molecular weight was equal to that of an extended chain produced by elimination of the fluorescence label from the end of the extended primer of Example 2, suggesting that fluorescence label of MRT was successfully removed after the primer extension.

EXAMPLE 5

Secondary MRT Extension via Polymerization with MRT Using DNA as a Primer

After removing a fluorescent group from the 3'-end as the same manner as described in Example 4, the obtained DNA was purified by reverse-phased HPLC. The purified DNA was used as a primer for the second extension reaction with the MRT. The extension was performed by the same manner as described in Example 2. The resultant product was characterized using MALDI-TOF mass spectrometry (FIG. 3d).

As a result, as shown in FIG. 3d, the extended primer prepared by polymerase in Example 4 was gone and instead molecular weight 7382 peak newly generated by the reaction of the primer and one molecule of 3'-O-(7-hydroxycoumarin)-dTTP was confirmed (FIG. 3). This molecular weight was equal to that of an extended chain produced by extension of primer of example 4 with compound 13 using polymerase, suggesting that the primer chain could be extended again by another MRT after the fluorescence label analysis and elimination.

Therefore, it was confirmed that sequencing-by-synthesis can be successfully carried out by polymerization based on the analysis of fluorescence signal at each extension stage.

INDUSTRIAL APPLICABILITY

The sequencing method (sequencing-by synthesis) of the present invention is efficient for continuous polymerization because there is no molecular scar remaining after fluorescent group elimination after fluorescence analysis, unlike the conventional SBS. In addition, the method of the present invention facilitates simultaneous elimination of fluorescence label and blocking group, providing high yield. Therefore, it can be effectively used for efficient and fast sequencing.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A nucleotide monomer having a physically or a chemically removable reversible fluorescent blocking group on a 3'-OH moiety of a nucleoside triphosphate in a compound represented by Formula 2:

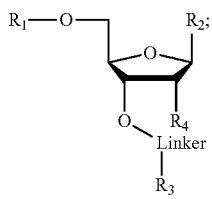

wherein:
- $R_1$ is triphosphate;
- $R_2$ is nucleobase;
- $R_4$ is H or OH; and
- the linker-$R_3$ is selected from the group consisting of the fluorescent blocking groups having the following chemical structures:

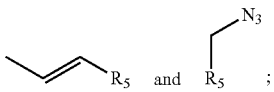

wherein $R_5$ is fluorophore.

2. The nucleotide monomer according to claim 1, wherein the compound has the following chemical structure:

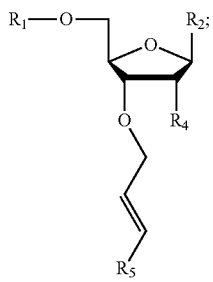

wherein
- $R_1$ is triphosphate;
- $R_2$ is nucleobase;
- $R_4$ is H or OH; and
- $R_5$ is fluorophore.

3. The nucleotide monomer according to claim 2, wherein the fluorophore is selected from the group consisting of coumarin, AlexaFluor, Bodipy, fluorescein, tetramethylrhodamine, Cy5, Cy3, Texas Red, and their derivatives.

4. The nucleotide monomer according to claim 1, wherein the compound has the following chemical structure:

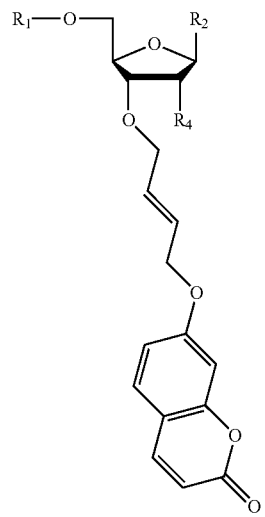

wherein
- $R_1$ is triphosphate;
- $R_2$ is nucleobase; and
- $R_4$ is H or OH.

5. A sequencing method comprising the following steps:
1) synthesizing the nucleotide monomer of claim 1;
2) preparing a nucleotide chain of interest as template and a primer
3) incorporating one nucleotide monomer of step 1) into the primer of step 2) by a DNA or an RNA polymerase, resulting in an extended primer;
4) identifying a base of the extended primer by detecting fluorescence signal from the fluorescent blocking group conjugated to a 3'-OH moiety of the extended primer resulted from the incorporating of step 3);
5) removing the fluorescent blocking group from the extended primer of step 4) and then restoring a free 3'-OH group to continue incorporation of the nucleotide monomer of step 1); and
6) repeating steps from 3) to 5) to sequence a target template.

6. The sequencing method according to claim 5, wherein the template of step 2) is selected from the group consisting of genomic DNAs, plasmids and oligonucleotides.

7. The sequencing method according to claim 5, wherein the polymerase of step 3) is selected from the group consisting of a thermophilic polymerase, a mesophilic polymerase and its mutant.

8. The sequencing method according to claim 5, wherein the fluorescence signal of step 4) is detected by measuring fluorescence of a solid phase on which the double stranded DNA of template and the primer is immobilized or by measuring fluorescence of solution containing the double stranded DNA.

9. The sequencing method according to claim 5, wherein the fluorescent blocking group of step 5) is preferably removed by using Pd catalyst, tris-alkylphosphine, tris-arylphosphine or their derivatives.

10. A sequencing kit for sequencing-by-synthesis (SBS) containing the nucleotide monomer of claim 1 or its multimer.

11. The nucleotide monomer according to claim 1, wherein the fluorophore is selected from the group consisting of coumarin, AlexaFluor, Bodipy, fluorescein, tetramethylrhodamine, Cy5, Cy3, Texas Red, and their derivatives.

12. The nucleotide monomer according to claim 1, wherein the compound has the following chemical structure:

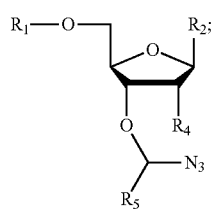

wherein $R_1$ is triphosphate;

$R_2$ is nucleobase;

$R_4$ is H or OH; and $R_5$ is fluorophore.

13. The nucleotide monomer according to claim 12, wherein the fluorophore is selected from the group consisting of coumarin, AlexaFluor, Bodipy, fluorescein, tetramethylrhodamine, Cy5, Cy3, Texas Red, and their derivatives.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
gctacgactc actatggacg                                              20

<210> SEQ ID NO 2
<211> LENGTH: 30
```

```
<212> TYPE: DNA
<213> ORGANISM: Artificial
<220> FEATURE:
<223> OTHER INFORMATION: template

<400> SEQUENCE: 2
aaaaaaaaaa cgtccatagt gagtcgtagc                                    30
```